(12) United States Patent
Huegerich

(10) Patent No.: US 11,446,508 B2
(45) Date of Patent: Sep. 20, 2022

(54) IMPLANTABLE MEDICAL DEVICE CONFIGURED TO ESTABLISH A COMMUNICATION LINK TO ANOTHER IMPLANTABLE MEDICAL DEVICE

(71) Applicant: BIOTRONIK SE & CO. KG, Berlin (DE)

(72) Inventor: Burkhard Huegerich, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 261 days.

(21) Appl. No.: 16/990,392

(22) Filed: Aug. 11, 2020

(65) Prior Publication Data

US 2021/0085989 A1    Mar. 25, 2021

Related U.S. Application Data

(60) Provisional application No. 62/902,408, filed on Sep. 19, 2019.

(51) Int. Cl.
*A61N 1/37* (2006.01)
*H04M 1/72412* (2021.01)
(Continued)

(52) U.S. Cl.
CPC ..... *A61N 1/37288* (2013.01); *A61N 1/39622* (2017.08); *H04B 7/00* (2013.01); *H04M 1/72412* (2021.01)

(58) Field of Classification Search
CPC ........... A61N 1/37288; A61N 1/39622; H04M 1/72412; H04B 7/00
See application file for complete search history.

(56) References Cited

U.S. PATENT DOCUMENTS 7,280,872 B1 * 10/2007 Mosesov ............ A61N 1/37276
607/31
7,957,813 B1 * 6/2011 Persson ............. A61N 1/37276
607/32
(Continued)

FOREIGN PATENT DOCUMENTS

EP     2361654 A1    8/2011
EP     2327609 B1    1/2016
(Continued)

*Primary Examiner* — Hai V Nguyen
(74) *Attorney, Agent, or Firm* — Laurence A. Greenberg; Werner H. Stemer; Ralph E. Locher

(57) ABSTRACT

An implantable medical device, contains control circuitry and communication circuitry for communicating with another implantable medical device. The communication circuitry includes a transmission unit and a reception unit. The transmission unit, for establishing a communication link with the other implantable medical device, is configured to transmit a multiplicity of transmit communication signals, wherein each transmit communication signal is associated with a dedicated sub-range of a predefined frequency range. The reception unit is configured to receive a response communication signal in response to a transmit communication signal. The control circuitry is configured to determine whether a response communication signal in response to a transmit communication signal associated with a dedicated sub-range has been received, and to establish the communication link based on the determination.

13 Claims, 3 Drawing Sheets

(51) Int. Cl.
  *A61N 1/372* (2006.01)
  *A61N 1/39* (2006.01)
  *H04B 7/00* (2006.01)

(56) References Cited

U.S. PATENT DOCUMENTS

| | | | |
|---|---|---|---|
| 3,342,598 | A1 | 1/2013 | Stanton |
| 8,423,139 | B2 * | 4/2013 | Zhu ................ A61N 1/371 |
| | | | 607/9 |
| 8,805,528 | B2 | 8/2014 | Corndorf |
| 9,008,768 | B2 * | 4/2015 | Zhu ................ A61N 1/371 |
| | | | 607/9 |
| 10,091,784 | B1 * | 10/2018 | Liu .................... H04J 11/00 |
| 10,307,600 | B2 * | 6/2019 | Ney ................... G16H 40/63 |
| 10,485,444 | B2 * | 11/2019 | Axelrod ............. A61B 5/392 |
| 10,512,414 | B2 * | 12/2019 | Axelrod ............. A61B 5/296 |
| 10,921,456 | B2 * | 2/2021 | He ................... G01S 19/243 |
| 2006/0135998 | A1 * | 6/2006 | Libbus ............ A61N 1/36117 |
| | | | 607/2 |
| 2007/0239210 | A1 * | 10/2007 | Libbus ............ A61N 1/36114 |
| | | | 607/2 |
| 2010/0030303 | A1 * | 2/2010 | Haubrich .......... A61N 1/37252 |
| | | | 607/60 |
| 2011/0130802 | A1 * | 6/2011 | Libbus ............ A61N 1/36114 |
| | | | 607/17 |
| 2012/0035682 | A1 * | 2/2012 | Libbus ............ A61N 1/36114 |
| | | | 607/28 |
| 2013/0085550 | A1 * | 4/2013 | Polefko ............ A61N 1/37252 |
| | | | 607/59 |
| 2016/0121129 | A1 * | 5/2016 | Persson ............ A61N 1/37288 |
| | | | 607/32 |
| 2016/0294486 | A1 * | 10/2016 | Bolin .................... H04L 5/0048 |
| 2019/0372648 | A1 * | 12/2019 | Kinamon ............ H04L 5/0032 |
| 2020/0049829 | A1 * | 2/2020 | He ........................ G01S 19/02 |
| 2022/0182124 | A1 * | 6/2022 | Kinamon ............ H04B 7/0413 |

FOREIGN PATENT DOCUMENTS

| | | |
|---|---|---|
| WO | 2012056298 A2 | 5/2012 |
| WO | 2012056298 A3 | 5/2012 |

\* cited by examiner

IMPLANTABLE MEDICAL DEVICE CONFIGURED TO ESTABLISH A COMMUNICATION LINK TO ANOTHER IMPLANTABLE MEDICAL DEVICE

CROSS-REFERENCE TO RELATED APPLICATION

This application claims the benefit, under 35 U.S.C. § 119(e), of provisional patent application No. 62/902,408, filed Sep. 19, 2019; the prior application is herewith incorporated by reference in its entirety.

BACKGROUND OF THE INVENTION

Field of the Invention

The instant invention generally relates to an implantable medical device, a system of implantable medical devices, and a method for establishing a communication link in between an implantable medical device and another implantable medical device.

An implantable medical device of this kind may for example be a pacemaker, an implantable cardioverter defibrillator, a sensor device such as a pressure sensor, or a recording device such as a loop recorder to be subcutaneously implanted in a patient.

An implantable pacemaker may for example be subcutaneously implanted in a patient and may comprise leads carrying electrodes and extending from a generator unit of the pacemaker device into the patient's heart for example to provide a pacing action in the right ventricle of the heart. Alternatively, an implantable pacemaker device may be defined as a leadless pacemaker not comprising leads, but being directly implanted into the patient's heart, for example in the right ventricle in order to provide for a pacing action.

A cardioverter defibrillator may serve for monitoring and treating potentially life-threatening arrhythmias in a patient's heart, wherein a cardioverter defibrillator of this kind may for example be implanted subcutaneously and may comprise leads extending into the patient's heart in order to record signals and to inject stimulation energy into the patient's heart for example to provide an electric shock (defibrillation).

Sensor devices, such as pressure sensors, flow sensors, temperature sensors or the like, may for example be implanted into a blood vessel, such as a vein, in order to provide for a monitoring of relevant parameters in the context of providing a therapy.

A loop recorder is for example subcutaneously implanted and serves to continuously record information for example about cardiac activity, such as an ECG. A loop recorder may continuously loop its memory and may store particular portions of signals, such that recorded signals may be communicated to an external device for analyzing the signals and for providing a diagnosis.

There is a desire that medical devices implanted in a patient may communicate with each other in order to allow the medical devices to interact. For example, signals sensed by a pacemaker device or an implanted sensor device may be transmitted to a loop recorder such that the loop recorder may record such signals. In addition, a pacemaker device may receive signals from a sensor device implanted remotely from the pacemaker device in order to take sensing signals of the sensor device into account for controlling a pacing action in the patient's heart.

For establishing a communication, approaches exist to create an intra-body network (IBN) linking implanted medical devices with each other such that signals may be exchanged in between the implanted medical devices.

For example, European patent EP 2 327 609 B1 describes an acoustic communication link in between implanted medical devices for exchanging information in between the implanted medical devices. The acoustic communication link is established to permit wireless communication between the implanted medical devices, wherein transmission parameters may be adapted, such as a sensitivity and a carrier frequency, in order to improve an existing communication link.

A wireless communication in between implanted medical devices may generally involve acoustic, radio frequency (RF) or magnetic signals. Generally, herein, signals are transmitted using a particular carrier frequency, wherein a transmission may be initiated by one implantable medical device for reception by another medical device. If one medical device transmits a signal using a particular carrier frequency, it herein must be ensured that the other medical device is able to receive the signal on that carrier frequency. As implanted medical devices generally are small in size and hence may comprise only a simplified processing circuitry, it may be the case that an implanted medical device is not able to reliably tune to and maintain a particular carrier frequency, as it is required for a reliable communication link.

SUMMARY OF THE INVENTION

It is an object to provide an implantable medical device, a system of implantable medical devices and a method for establishing a communication link in between implantable medical devices allowing for a reliable establishing of a communication link for transmitting signals.

In one aspect, an implantable medical device comprises a control circuitry and a communication circuitry for communicating with another implantable medical device, the communication circuitry comprising a transmission unit and a reception unit. The transmission unit, for establishing a communication link with the other implantable medical device, is configured to transmit a multiplicity of transmit communication signals, wherein each transmit communication signal is associated with a dedicated sub-range of a predefined frequency range. The reception unit is configured to receive a response communication signal in response to a transmit communication signal. The control circuitry is configured to determine whether a response communication signal in response to a transmit communication signal associated with a dedicated sub-range has been received, and to establish the communication link based on the determination.

An implantable medical device, such as for example a sensor device, may be in a sleep mode over prolonged periods of time in case a full functioning of the implantable medical device is not required. In the sleep mode certain functions of the implantable medical device may be shut down, such as a communication function to communicate with other medical devices. Hence, at an initial power up of a medical device or after a phase in which the medical device has been in the sleep mode, a communication link with another medical device may have to be established in order to allow for a data communication between the medical devices.

In order to establish the communication link in the context of an intra-body network, a carrier frequency used by one medical device for transmission and reception of signals must match with a carrier frequency which the other medical device uses for reception and transmission. Only if the medical devices work on the same carrier frequency, a reliable communication link can be established in between the medical devices.

As in particular for small, low-power medical devices it cannot always be ensured that the medical device is able to reliably establish a carrier frequency with sufficient accuracy, it herein is proposed that medical devices negotiate a carrier frequency in the context of establishing a communication link, such that prior to a data communication it is defined which carrier frequency to use for the communication in between the medical devices.

For this, a medical device wishing to establish the communication link transmits different transmit communication signals towards another medical device, wherein each transmit communication signal is associated with a dedicated sub-range of a predefined frequency range. This assumes that a carrier frequency resides in a predefined frequency range, wherein it needs to be established which carrier frequency in the frequency range may be used by the medical devices in order to allow for a data communication.

For this, the predefined frequency range is divided into certain sub-ranges. The medical device wishing to establish the communication link sends out different transmit communication signals in the different sub-ranges in order to detect whether a response communication signal from the other medical device is received in any sub-range. Based on a response communication signal that has been received in response to a particular transmit communication signal, then, the control circuitry of the implantable medical device may establish the communication link, such that a carrier frequency within the sub-range for which a response has been received may be used for a data communication in between the medical devices.

In one embodiment, the transmission unit is configured to sequentially transmit, for establishing a communication link, transmit communication signals associated with a sequence of dedicated sub-ranges in said predefined frequency range. The medical device hence transmits a sequence of transmit communication signals, the transmit communication signals being associated with different sub-ranges such that the medical device is enabled to establish whether the other medical device is able to use any of those sub-ranges for a data communication.

In one embodiment, the transmission unit is configured to sequentially transmit, for establishing a communication link, transmit communication signals starting at a sub-range at a first end of the frequency range, and ending at a sub-range at a second end of the frequency range opposite the first end. The medical device, by transmitting a sequence of transmit communication signals, hence performs a frequency sweep starting for example at a lower end of the defined frequency range in order to successively increase the frequency until a second, upper end of the frequency range is reached. It herein may be detected whether a response in one or multiple of the sub-ranges is received by the other medical device, such that a communication link may be established based on such response communication signal.

This concept of sweeping through a pre-defined range of sub-frequencies can be utilized in a sequence of subsequently defined narrower bands of sub-frequencies thus allowing for a very fine tuning of the utilized communication frequency with the result of an optimized communication link between implanted devices.

In one embodiment, the reception unit is configured to record, after each transmission of a transmit communication signal, a received response communication signal. Hence, the medical device monitors whether a response to a particular transmit communication signal is received, such that based on the response it can be determined whether the other medical device is able to communicate in the particular sub-range associated with a transmit communication signal. By means of the response the other medical device acknowledges the reception of the transmit communication signal, and by the response communication signal informs the (first) medical device that it is able to communicate making use of a carrier frequency in the sub-range associated with the particular transmit communication signal and response communication signal.

The transmit communication signal and likewise the response communication signal may for example be modulated using a common modulation scheme, such as a PCM, FSK, PSK, QPSK, FM or AM modulation or the like. In the transmit communication signal, herein, an identifier of the other medical device to which a communication link shall be established and an identifier of the transmitting medical device may be encoded, in addition to a trigger message (such as a "Hello" message) informing the other medical device that that a communication link shall be established. The other medical device is able to decode the transmit communication signal and to create a response communication signal, in which for example an identifier of the medical device seeking communication, an identifier of the responding medical device and an acknowledgment message (such as an "OK" message) is encoded.

For each sub-range, herein, the transmission of the transmit communication signal may take place once, or may be repeated for a predefined number of times, for example four times.

In one embodiment, the control circuitry is configured to select a sub-range for establishing the communication link if a response communication signal is received in response to a transmit communication signal associated with the sub-range. Generally, if a response in a particular sub-range is received, it is assumed that the other medical device is able to communicate in that sub-range. The control circuitry hence may choose the sub-range for establishing the communication link.

Different scenarios may exist herein.

If, in the context of the frequency sweep, a response signal is received in a particular sub-range, the medical device may transmit another transmit communication signal in a subsequent, adjacent sub-range. If no response signal is received in the subsequent sub-range, the control circuitry of the medical device may cause the frequency sweep to end and may choose the particular, previous sub-range in which the response signal has been received for establishing the communication link.

If a response signal, in another example, is received in a particular sub-range, and one or multiple further response signals in one or multiple further sub-ranges are received, the control circuitry may choose one of the sub-ranges to establish the communication link. If for example response signals in three consecutive sub-ranges have been received, the control circuitry may choose the middle sub-range of these sub-ranges for establishing the communication link.

If a response signal, in another example, is received in a particular sub-range, and one or multiple further response signals in one or multiple further sub-ranges are received, the control circuitry may choose one of the sub-ranges to establish the communication link. If for example response signals in three consecutive sub-ranges have been received and each sub-range was tested e.g. with 4 "Hello" messages but only one sub-range responded to all 4 "Hello" messages with an "OK" response and the other responded to less than 4 "Hello" messages with an "OK" message, the control circuitry may choose the sub-range of these sub-ranges which resulted in receiving 4 "OK" messages for establishing the communication link.

If neither of the selected sub-ranges achieves an "OK" response to all "Hello" messages, the control circuitry may choose the perform an additional sweep with a fine grade sub-range within the previous sub-range which resulted in receiving the most "OK" messages to subsequently identifying the optimal carrier frequency for establishing the communication link.

If, in the context of the frequency sweep, no response communication signal is received by the medical device for any transmit communication signal associated with any sub-range, the control circuitry may be configured to terminate the establishing of the communication link with the other implantable medical device. Hence, if no response from the other medical device can be received, it is assumed that at this time no communication link with the other medical device can be established, such that no further transmit communication signals for establishing the communication link are sent out.

Herein, after a certain time period, for example a few minutes, the medical device may retry to establish the communication link with the other medical device by repeating the negotiation procedure.

The medical device generally may make use of different transmission technologies in order to provide for a communication with another medical device. In particular, signals may be transmitted and received using an acoustic transmission, a radiofrequency (RF) transmission, a magnetic (inductive) transmission, or a purely electric field transmission.

If for example a transmission is employed, it may be advantageous to use a carrier frequency in a rather low frequency range, such as in between 10 kHz and 1 MHz, preferably in between 300 kHz and 500 kHz, for example around 400 kHz. As signals have to be transmitted through human tissue, signals may experience losses, such that a transmission at a rather low frequency (and a correspondingly large wavelength) is preferable over a transmission with higher frequencies. For the transmission, oscillating electric fields may be used which will induce electric potential fluctuations throughout the body due to electrolytes in bodily fluids.

In another aspect, a system of implantable medical devices comprises a first implantable medical device and a second implantable medical device. The first implantable medical device comprises a first control circuitry and a first communication circuitry having a first transmission unit and a first reception unit. The second implantable medical device comprises a second communication circuitry having a second transmission unit and a second reception unit. The first transmission unit, for establishing a communication link with the second implantable medical device, is configured to transmit a multiplicity of transmit communication signals, wherein each transmit communication signal is associated with a dedicated sub-range of a predefined frequency range. The second reception unit is configured to receive a transmit communication signal of said multiplicity of transmit communication signals. The second transmission unit is configured to transmit, in response to receiving the transmit communication signal, a response communication signal. The first transmit reception unit is configured to receive said response communication signal. The first control circuitry is configured to determine whether a response communication signal in response to a transmit communication signal associated with a dedicated sub-range has been received, and to establish the communication link based on the determination.

The advantages and advantageous embodiments described above for the medical device equally apply to the system, such that it shall be referred to the above description in this respect.

A first implantable medical device sends out transmit communication signals in order to establish a communication link to another, second medical device. The second medical device, by means of its reception unit, receives one or multiple of the transmit communication signals and generates, in reaction to a received transmit communication signal, a response communication signal in the sub-range to which the transmit communication signal is associated. The response communication signal, by means of the transmission unit of the second medical device, is sent to the first medical device, which receives the response communication signal and establishes a communication link based on the response communication signal. Hence, in a trigger/acknowledgment scheme a first medical device tries certain sub-ranges of a frequency range in order to establish a communication link. If a response in one of the sub-ranges is received, this is concluded to indicate that the other, second medical device is enabled to communicate in the particular sub-range, such that a communication link is established making use of a carrier frequency in the sub-range.

In yet another aspect, a method for establishing a communication link between an implantable medical device and another implantable medical device comprises transmitting, using a transmission unit of a communication circuitry of the implantable medical device, a multiplicity of transmit communication signals, wherein each transmit communication signal is associated with a dedicated sub-range of a predefined frequency range. A reception unit of the communication circuitry of the implantable medical device is used for receiving a response communication signal in response to a transmit communication signal. Control circuitry of the implantable medical device is used to determine whether a response communication signal in response to a transmit communication signal associated with a dedicated sub-range has been received. A communication link based on the determination is then established.

The advantages and advantageous embodiments described above for the implantable medical device and the system of implantable medical devices equally apply also to the method, such that it shall also be referred to the above.

Within the method, a frequency sweep over multiple sub-ranges within a frequency range may be performed. For this, in one embodiment, the step of transmitting multiple transmit communication signals may include a sequential transmission of transmit communication signals starting at a sub-range at a first end of the frequency range and ending at a sub-range at a second end of the frequency range. In one embodiment, at the start of the frequency sweep a first transmit communication signal may be transmitted in a first sub-range at the first end of the frequency range. Subsequently, a second transmit communication signal in a second sub-range adjacent the first sub-range may be transmitted. Further transmit communication signals in further, successive sub-ranges following the second sub-range may then be transmitted until a last sub-range at a second end of the frequency range opposite the first end is reached.

The sweep may start at the lower end of the frequency range and end at the upper end. Alternatively, the sweep may start at the upper end and may end at the lower end.

The frequency sweep may be terminated if a response communication signal is received in a sub-range, but no further response signal is received in a subsequent, adjacent sub-range.

The procedure for establishing a communication link may be carried out at any time a medical device wishes to establish a communication with another medical device. This may take place at an initial startup of the medical device or after exiting a phase of a sleep mode in which a communication function for example has been shut down.

As the sub-range to be used for communication is negotiated prior to establishing the communication link, the medical devices not necessarily have to comprise circuitry which is able to establish an exact, predefined carrier frequency with a high degree of accuracy. As the carrier frequency is negotiated prior to any communication, a circuitry of the medical devices may be simplified, and costs as well as power consumption may be reduced. Also, possibly a wider frequency range may be used for a communication.

The features disclosed in regard with the device and the system may also apply to the method and vice versa.

Other features which are considered as characteristic for the invention are set forth in the appended claims.

Although the invention is illustrated and described herein as embodied in an implantable medical device configured to establish a communication link to another implantable medical device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
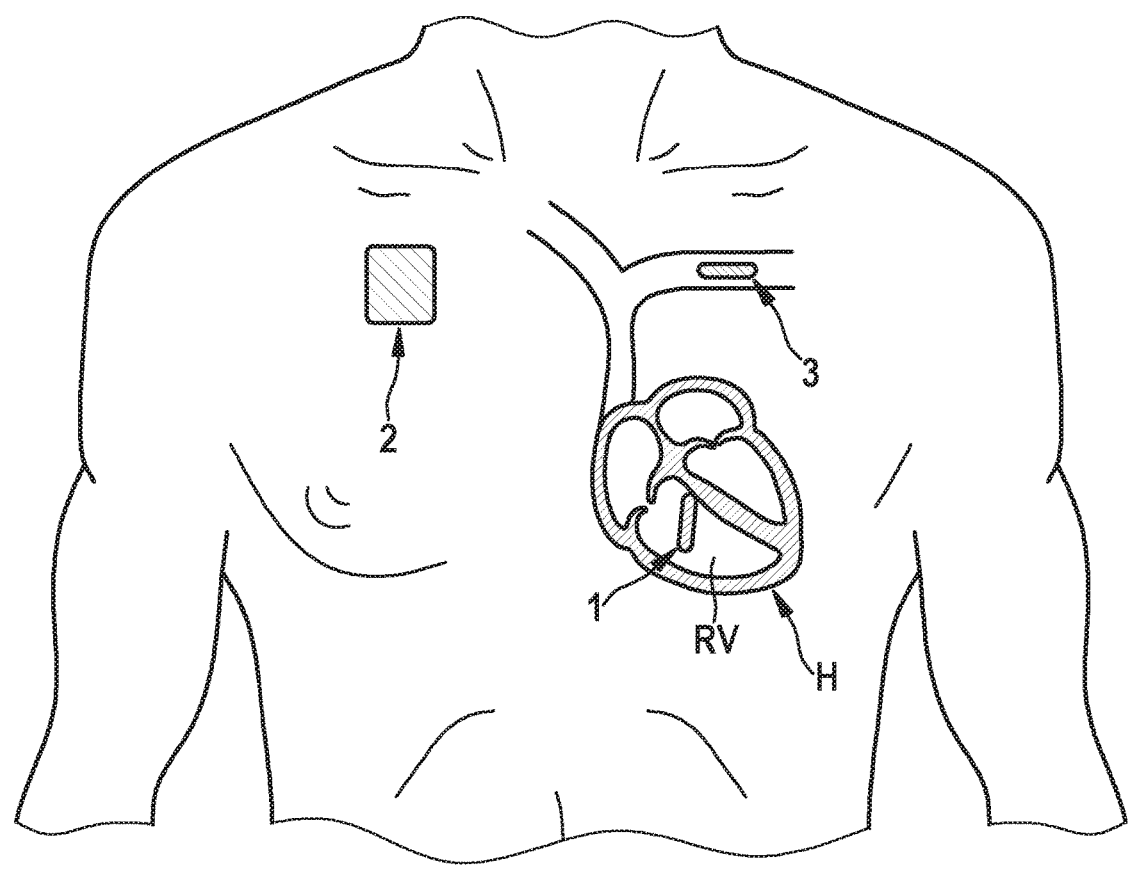
FIG. 1 is an illustration showing a system of medical devices implanted in a patient.

Subsequently, embodiments of the invention shall be described in detail with reference to the drawings. In the drawings, like reference numerals designate like structural elements.

It is to be noted that the embodiments are not limiting for the invention, but merely represent illustrative examples.

Referring now to the figures of the drawings in detail and first, particularly to FIG. 1 thereof, there is shown implantable medical devices 1, 2, 3 may be implanted in a patient at different locations in order to provide different functions within the patient. For example, a medical device 1 in the shape of a leadless pacemaker device may be implanted in the right ventricle RV of the patient's heart in order to provide for a pacing action within the heart H. Another medical device 2 for example in the shape of a loop recorder may subcutaneously be implanted within the chest, the loop recorder allowing for a recording of signals and, for example, a communication with an external device in order to monitor certain parameters within the patient. Another implantable medical device 3 in the shape of a sensor device, for example a pressure sensor, a flow sensor or a temperature sensor or the like, may be implanted for example in a blood vessel in order to sense characteristic parameters such as a blood pressure or a blood flow.

There generally exists a desire for a data communication in between different medical devices 1, 2, 3 implanted in a patient. Approaches exist to establish a communication of this kind in a wireless fashion by establishing an intra-body network linking the medical devices 1, 2, 3 together, such that data may be exchanged in between the medical device 1, 2, 3. A loop recorder may hence for example record sensor data of a sensor device, or data of a pacemaker or a cardioverter defibrillator, and may also provide data for example to a pacemaker or a cardioverter defibrillator to control a therapeutic action.

In order to allow for a data communication, a communication link between medical devices 1, 2, 3 needs to be established. Signals herein are exchanged in a modulated fashion making use of a particular transmission technology, such as an acoustic transmission, radio frequency (RF) transmission, a magnetic (inductive) signal transmission, or an oscillating electric field based transmission, and a particular modulation scheme, such as a PCM, FSK, PSK, QPSK, FM, or AM modulation or the like.

Regardless of the specific transmission technology, transmission takes place by employing a carrier frequency, which must match in between the communicating medical devices 1, 2, 3 in order to establish a reliable communication link.

Figure 2:
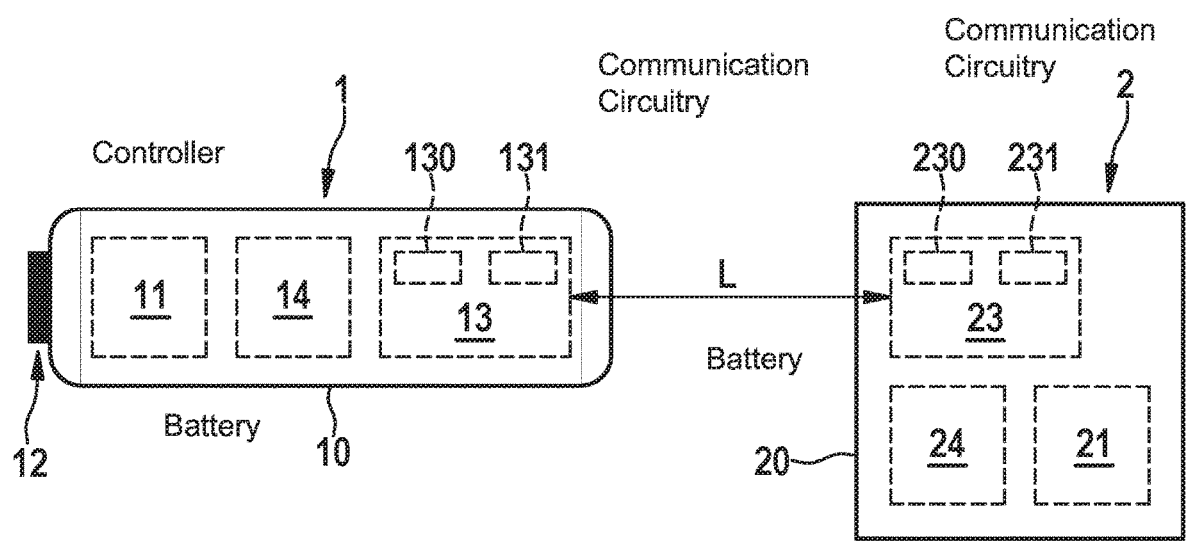
FIG. 2 is a block diagram of two medical devices in between which a communication link for a data communication in between the medical devices shall be established.

Referring now to FIG. 2, medical devices 1, 2 to be implanted in a patient may have a small built and may be designed for a low power consumption in order to remain in a patient over a long-term.

The first medical device 1, for example in the shape of a leadless pacemaker, may herein comprise a housing 10, a control circuitry 11, an electrode arrangement 12 for emitting stimulation signals, or receiving sense signals, a communication circuitry 13 and an energy storage 14, for example in the shape of a battery.

A second medical device 2, for example in the shape of an implantable sensor device, such as a pressure sensor, or in the shape of a loop recorder, comprises a housing 20, a control circuitry 21, a communication circuitry 23, and an energy storage 24, for example in the shape of a battery.

The communication circuitry 13, 23, in each case, comprises a transmission unit 130, 230, and a reception unit 131, 231. The communication circuitry 13, 23, is designed for the specific transmission technology, which is for transmitting and receiving of acoustic signals, radio frequency (RF) signals, magnetic signals or electrical signals. Also, the communication circuitry 13, 23 is configured to modulate respectively demodulate signals for transmission and reception, to optimize transmission parameters, to amplify received signals and to process signals in order to forward processed signals to the control circuitry 11, 21 for an analysis and control of the operation of the medical device 1, 2.

The communication circuitry 13, 23 is in particular enabled to modify a carrier frequency for transmission, as shall be explained in detail below.

A communication link L shall be established in between the medical devices 1, 2 for example at the initial startup of one of the medical devices 1, 2 or after exiting a sleep mode after a prolonged duration of passivity of the medical device 1, 2. Herein, a medical device 1, 2 which wishes to establish a communication sends out a trigger signal towards the other medical device 2, 1, the trigger signal indicating that the medical device 1 wishes to establish communication.

In the context of establishing the communication link L, herein also a common carrier frequency to be used for the communication shall be negotiated in between the medical devices 1, 2. For this, the medical device 1, 2 wishing to establish the communication sends out a sequence of transmit communication signals over a frequency range and awaits response communication signals in order to then establish the communication link L making use of a carrier frequency in a particular sub-range of the frequency range.

Figure 3:
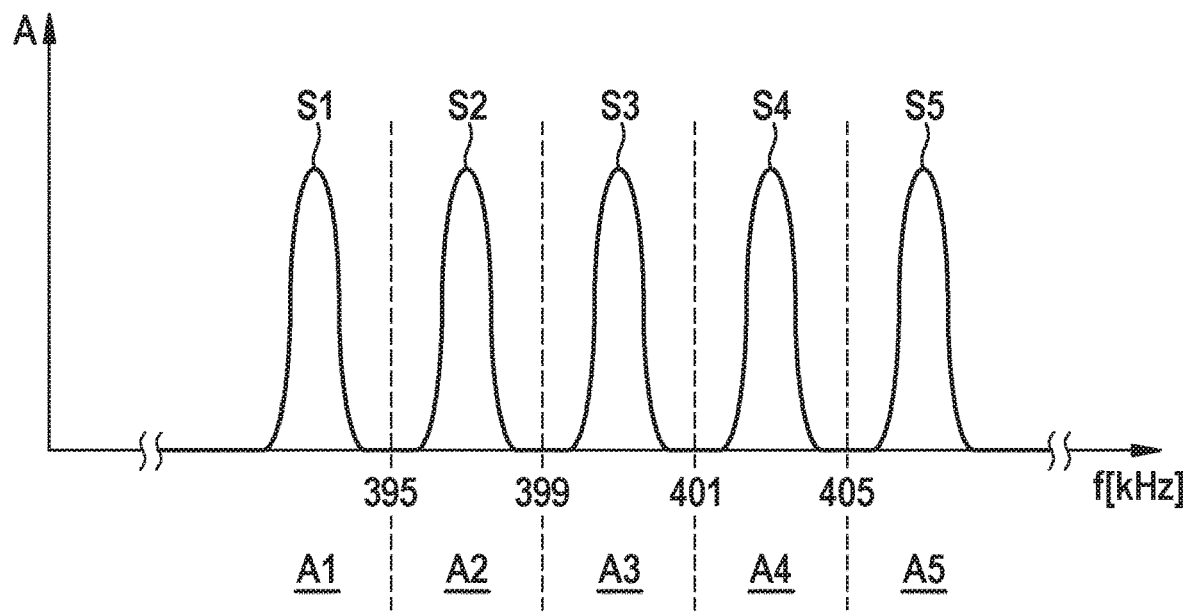
FIG. 3 is a graph showing a frequency range divided into sub-ranges and transmit communication signals associated with the sub-ranges.

Referring now to FIG. 3, a frequency range in which a communication may be established may for example be centered around a center frequency of 400 kHz. For example, a frequency range may range from a lower frequency at about 380 kHz to an upper frequency at about 420 kHz. It herein is assumed that a central sub-range A3 in between 399 kHz and 401 kHz is optimal for communication, wherein a communication may also be established in other sub-ranges A1, A2, A4, A5, corresponding to a sub-range A1 below 395 kHz, a sub-range A2 in between 395 kHz and 399 kHz, a subrange A4 in between 401 kHz and 405 kHz, and sub-range A5 above 405 kHz.

Hence, to establish a communication link L, the medical device 1, 2 wishing to establish the communication sends out transmit communication signals S1-S5 in the different sub-ranges A1-A5 and monitors whether a response communication signal in any of the sub-ranges A1-A5 is received from the other medical device 2, 1. The medical device 1, 2 herein, in one embodiment, performs a frequency sweep in that transmit communication signals S1-S5 are sequentially and consecutively transmitted starting at the lowest sub-range A1 and ending at the highest sub-range A5, wherein in each sub-range A1-A5 it is monitored whether a response communication signal from the other medical device 2, 1 is received.

Figure 4:
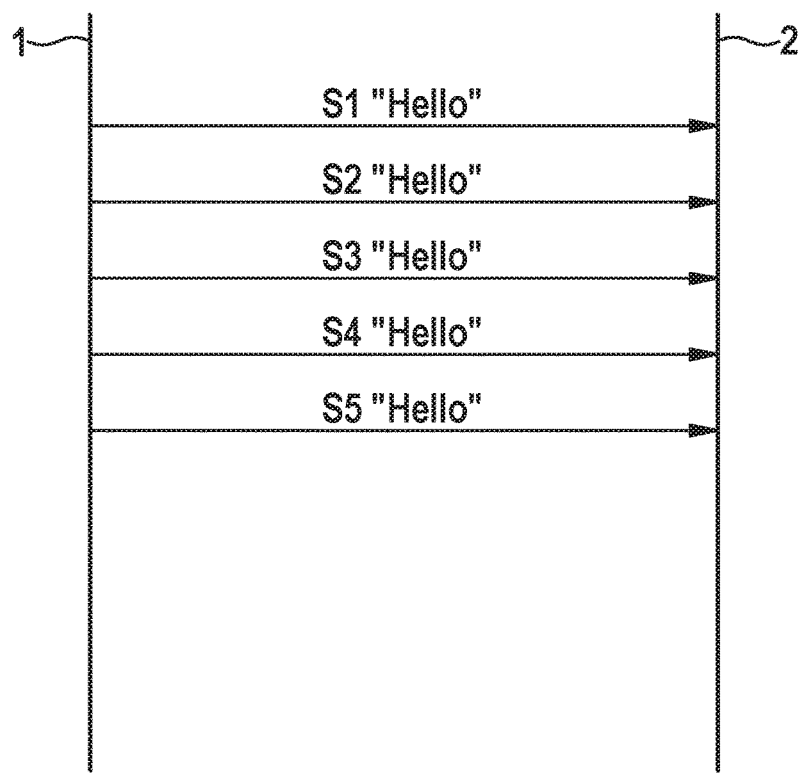
FIG. 4 is a schematic drawing showing a transmission of transmit communication signals from one medical device to another for establishing a communication link.

Referring now to FIG. 4, in one example the medical device 1 may sent out transmit communication signals S1-S5 to the other medical device 2. The transmit communication signals S1-S5 may be modulated messages comprising an identifier of the other medical device 2 with which a communication shall be established, and also comprising a trigger message ("Hello") notifying the other medical device 2 that a communication shall be established. Furthermore, the transmit communication signals S1-S5 may comprise an identifier of the sending medical device 1 such that the other medical device 2 is notified which device wishes to establish a communication.

Starting at the sub-range A1, the medical device 1 transmits, by means of the transmission unit 130, transmit communication signals S1-S5. The transmission of each transmit communication signal S1-S5 may herein be carried out once, or may be repeated for a predefined number of times, for example four times.

After each transmission the medical device 1 monitors whether a response signal is received from the other medical device 2, wherein the monitoring may take place over a predefined amount of time, i.e., a predefined waiting period in which the reception unit 131 awaits a response communication signal from the other medical device 2. If no response is received for a specific transmit communication signal S1-S5, the medical device 1 may go on to transmit a transmit communication signal S1-S5 in another, adjacent sub-range, until the end of the frequency range, i.e., the highest sub-range A5, is reached.

If, as in the example of FIG. 4, no response communication signals are received from the other medical device 2, the control circuitry 11 of the medical device 1 terminates the establishing of the communication link L, wherein, possibly, after a predetermined amount of time, for example a few minutes, it may be retried to establish a communication link L.

Figure 5:
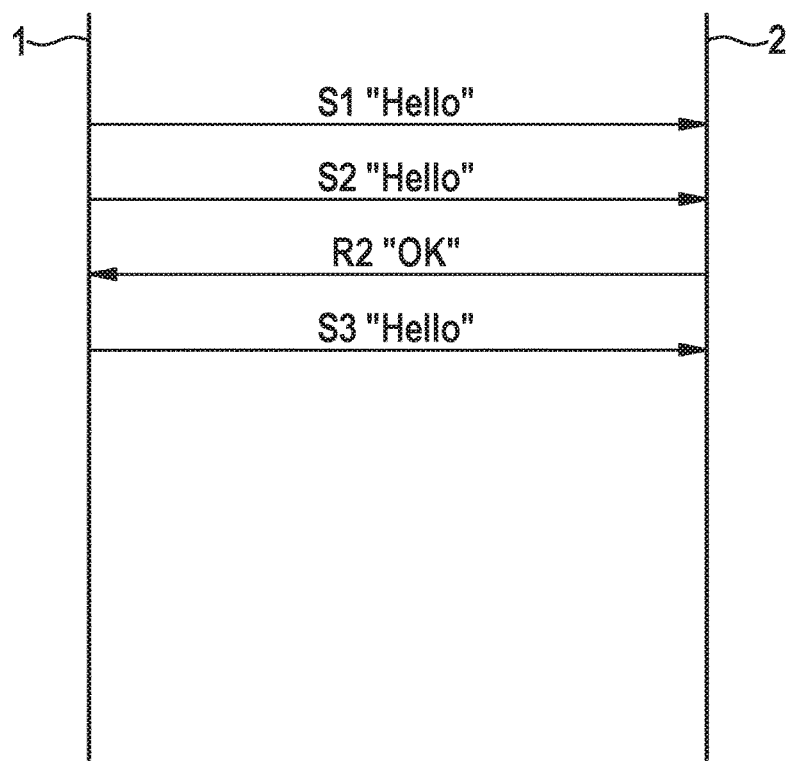
FIG. 5 is an illustration showing another example of a transmission of transmission communication signals.

Referring now to FIG. 5, if—following a transmit communication signal S2 associated with a particular sub-range A2—a response communication signal R2 is received, the medical device 1 may send out another transmit communication signal S3 in an adjacent sub-range A3 and monitor whether a response is also received in the adjacent sub-range A3. If this is not the case, the control circuitry 11 establishes a communication link L making use of a carrier frequency in the sub-range A2 in which a response communication signal R2 has been received.

The response communication signal R2 may for example comprise an identifier of the sending medical device 2, an identifier of the medical device 1 to which the response communication signal is directed, and an acknowledgment message ("OK") notifying the medical device 1 that the transmit communication signal S2 has been received and herewith is acknowledged.

Figure 6:
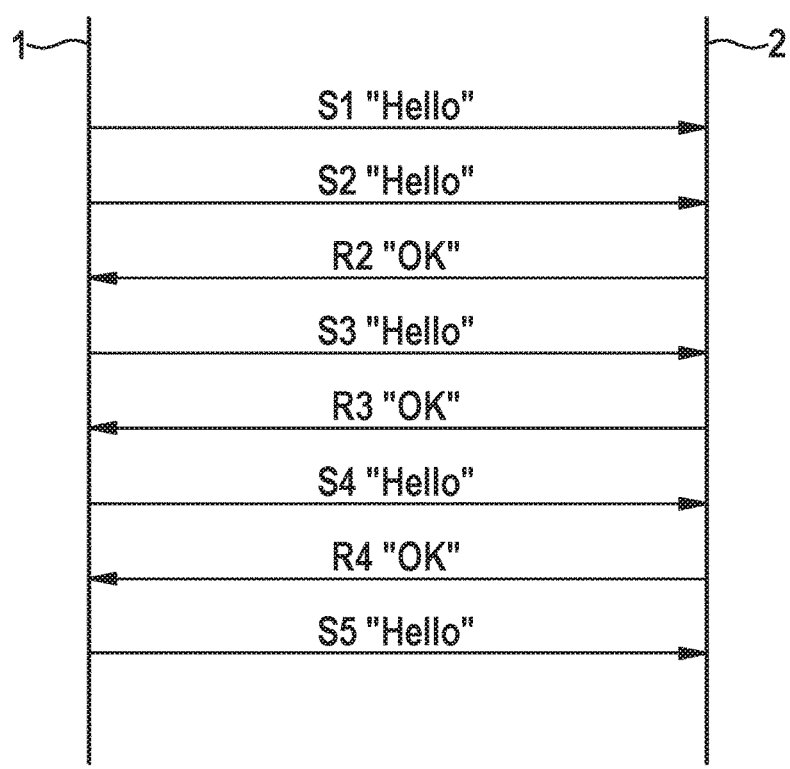
FIG. 6 is an illustration showing yet another example of a transmission of transmit communication signals for establishing a communication link.

Referring now to FIG. 6, in another example response communication signals R2, R3, R4 may be received for multiple transmit communication signals S2, S3, S4. Herein, the medical device 1 may continue to send out transmit communication signals S1-S5 until no further response communication signal R2-R4 is received or until the end of the frequency range, i.e., the highest sub-range A5, is reached.

If, as in the example of FIG. 6, multiple response communication signals R2-R4 are received, the control circuitry 11 may be configured to choose one of the sub-ranges A2-A4 associated with the response communication signals R2-R4 in order to establish the communication link L. For example, the middle sub-range A3 of the consecutive sub-ranges A2-A4 for which a response has been received may be selected. Or, if a response in the central, presumably optimal sub-range A3 is received, the sub-range A3 may always be chosen over all other sub-ranges A1, A2, A4, A5.

Because a carrier frequency to be used for a communication is negotiated in between the medical devices 1, 2, 3 prior to establishing the actual communication, medical devices 1, 2, 3 do not need to be able to accurately tune to a predefined frequency, but may use variable carrier frequencies within a frequency range. This allows to potentially simplify circuitry of the medical devices 1, 2, 3, and to reduce power consumption and costs.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE NUMERALS 1, 2, 3 Implantable medical device
10, 20 Housing
11, 21 Control circuitry
Electrode arrangement
13, 23 Communication circuitry
130, 230 Transmission unit
131, 231 Reception unit
14, 24 Energy storage
A1-A5 Sub-range
H Heart
L Communication link
RV Right ventricle
R2-R4 Response communication signal
S1-S5 Transmit communication signal

The invention claimed is:

1. An implantable medical device, comprising:
   control circuitry;
   communication circuitry for communicating with another implantable medical device, said communication circuitry having a transmitter and a receiver, said transmitter, for establishing a communication link with the other implantable medical device, is configured to transmit a plurality of transmit communication signals, wherein each of the transmit communication signals is associated with a dedicated sub-range of a predefined frequency range;
   said receiver is configured to receive a response communication signal in response to a transmit communication signal; and
   said control circuitry is configured to determine whether the response communication signal in response to the transmit communication signal associated with the dedicated sub-range has been received, and to establish the communication link based on a determination.

2. The implantable medical device according to claim 1, wherein said transmitter is configured to sequentially transmit, for establishing the communication link, the transmit communication signals associated with a sequence of dedicated sub-ranges in the predefined frequency range.

3. The implantable medical device according to claim 1, wherein said transmitter is configured to sequentially transmit, for establishing the communication link, the transmit communication signals starting at a dedicated sub-range at a first end of the predefined frequency range, and ending at a dedicated sub-range at a second end of the predefined frequency range opposite the first end.

4. The implantable medical device according to claim 1, wherein said receiver is configured to record, after each transmission of the transmit communication signal, the response communication signal received.

5. The implantable medical device according to claim 1, wherein said control circuitry is configured to select a dedicated sub-range for establishing the communication link if the response communication signal is received in response to the transmit communication signal associated with the dedicated sub-range.

6. The implantable medical device according to claim 1, wherein said control circuitry is configured to terminate an establishing of the communication link with the other implantable medical device if no said response communication signal for any said transmit communication signal is recorded by said receiver.

7. The implantable medical device according to claim 1, wherein the predefined frequency range lies within a region in between 10 kHz and 1 MHz.

8. The implantable medical device according to claim 1, wherein the predefined frequency range lies within a region in between 300 kHz and 500 kHz.

9. A system of implantable medical devices, comprising:
   a first implantable medical device having first control circuitry and first communication circuitry with a first transmitter and a first receiver;
   a second implantable medical device having second communication circuitry with a second transmitter and a second receiver;
   said first transmitter, for establishing a communication link with said second implantable medical device, is configured to transmit a plurality of transmit communication signals, wherein each transmit communication signal is associated with a dedicated sub-range of a predefined frequency range;
   said second receiver is configured to receive the transmit communication signal of the plurality of transmit communication signals;
   said second transmitter is configured to transmit, in response to receiving the transmit communication signal, a response communication signal;
   said first receiver is configured to receive the response communication signal; and
   said first control circuitry is configured to determine whether the response communication signal in response to the transmit communication signal associated with the dedicated sub-range has been received, and to establish the communication link based on a determination.

10. A method for establishing a communication link between an implantable medical device and another implantable medical device, which comprises the steps of:
    transmitting, using a transmitter of communication circuitry of the implantable medical device, a plurality of transmit communication signals, wherein each of the transmit communication signals is associated with a dedicated sub-range of a predefined frequency range;
    receiving, using a receiver of the communication circuitry of the implantable medical device, a response communication signal in response to a transmit communication signal; and
    determining, using control circuitry of the implantable medical device, whether the response communication signal in response to the transmit communication signal associated with the dedicated sub-range has been received, and establishing the communication link based on a determination.

11. The method according to claim 10, wherein the transmitting step includes: sequentially transmitting the transmit communication signals starting at a dedicated sub-range at a first end of the predefined frequency range.

12. The method according to claim 11, wherein the transmitting step further includes: transmitting a first transmit communication signal in a first dedicated sub-range at the first end of the predefined frequency range, subsequently transmitting a second transmit communication signal in a second dedicated sub-range adjacent the first sub-range.

13. The method according to claim 12, wherein the transmitting step further includes: transmitting the transmit communication signals in further dedicated sub-ranges following the second dedicated sub-range until a last dedicated sub-range at a second end of the predefined frequency range opposite the first end is reached.

* * * * *